United States Patent
Glatzer et al.

(10) Patent No.: US 8,097,743 A0
(45) Date of Patent: Jan. 17, 2012

(54) PROCESS FOR MANUFACTURE OF BLOCKED MERCAPTOSILANE COUPLING AGENTS

(75) Inventors: Holger Jürgen Glatzer, Parkersburg, WV (US); Beth Ann Raper, Sardis, OH (US)

(73) Assignee: Momentive Performance Materials Inc., Albany, NY (US)

( * ) Notice: Subject to any disclaimer, the term of this patent is extended or adjusted under 35 U.S.C. 154(b) by 402 days.

(21) Appl. No.: 10/697,919

(22) Filed: Oct. 30, 2003

(65) Prior Publication Data

US 2005/0245754 A1    Nov. 3, 2005

Related U.S. Application Data

(60) Provisional application No. 60/423,577, filed on Nov. 4, 2002.

(51) Int. Cl.
*C07F 7/02*    (2006.01)

(52) U.S. Cl. ...................................... 556/427; 556/428
(58) Field of Classification Search .................. 556/427, 556/428
See application file for complete search history.

(56) References Cited

U.S. PATENT DOCUMENTS

| | | | |
|---|---|---|---|
| 4,152,347 | A | 5/1979 | Pletka et al. |
| 4,222,930 | A | 9/1980 | Pletka et al. |
| 5,405,985 | A | 4/1995 | Parker et al. |
| 6,294,683 | B1 | 9/2001 | Johnson et al. |
| 6,384,255 | B1 | 5/2002 | Backer et al. |
| 6,384,256 | B1 | 5/2002 | Backer et al. |
| 6,414,061 | B1 | 7/2002 | Cruse et al. |
| 6,448,426 | B1 | 9/2002 | Backer et al. |
| 2003/0130388 | A1 | 7/2003 | Luginsland et al. |

FOREIGN PATENT DOCUMENTS

| | | |
|---|---|---|
| FR | 2375243 | 7/1978 |
| JP | 2003-201295 | 7/2003 |
| WO | 99/09036 | 2/1999 |

*Primary Examiner* — Daniel Sullivan
*Assistant Examiner* — Yevegeny Valenrod
(74) *Attorney, Agent, or Firm* — Dominick G. Vicari; Joseph S. Ostroff

(57) ABSTRACT

Blocked mercaptosilanes can be manufactured by reacting mercaptosilanes with organic or inorganic halides or anhydrides in the presence of an acid acceptor and washing the resulting reaction product with water/brine to yield two immiscible phases: an organic phase containing blocked mercaptosilane product and an aqueous phase containing the salt of the acid acceptor. Recycle of the acid acceptor is achieved by adding base to the aqueous phase. The process is suitable to be run in either batch or continuous mode. The blocked mercaptosilane compounds are used as coupling agents in rubber mixtures.

12 Claims, No Drawings

PROCESS FOR MANUFACTURE OF BLOCKED MERCAPTOSILANE COUPLING AGENTS

CROSS REFERENCE TO RELATED APPLICATIONS

This application claims priority on U.S. Provisional Application Ser. No. 60/423,577, filed on Nov. 4, 2002.

FIELD OF THE INVENTION

This invention describes a process to manufacture blocked mercaptosilanes from mercaptosilanes and reactive organic or inorganic halides or anhydrides in the presence of an acid acceptor. By addition of a polar phase, the sulfur-containing organosilicon compound can be separated from the [acid+ acid acceptor] phase that is formed upon addition. Recycle of the acid acceptor is achieved by adding a base to the [acid+ acid acceptor] phase. The process is suitable to be run in either batch or continuous mode. The compounds are used as coupling agents in rubber mixtures.

BACKGROUND OF THE INVENTION

The title compounds are mercaptosilane derivatives in which the mercapto group is blocked, i.e., the mercapto hydrogen is replaced by another group, the so-called blocking group. Of specific interest are thioester-containing organosilicon compounds that can be prepared by reacting a mercaptosilane with organic or inorganic halides or anhydrides, and in particular thiocarboxylic organosilicon compounds that have been identified as suitable coupling agents in the manufacture of silica-filled rubber mixtures (U.S. Pat. No. 6,414,061). Thiocarboxylic silanes are prepared from mercaptosilanes and preferably acid chlorides. The by-product in this reaction, anhydrous hydrogen chloride, triggers a number of unfavorable side reactions, including the transesterification of ethoxysilanes to mixed chloroethoxysilanes or even chlorosilanes. These reactions are very fast and cannot be prevented by manipulating common process parameters, e.g., temperature or pressure. It is possible, but technically very difficult, to restore the Si—OEt group (by means of a neutralization procedure). A much better way to run these reactions is to in situ neutralize HCl on a molecular level by means of an acid acceptor. This reaction is faster than the transesterification reaction and leads to very little formation of Si—Cl groups. Challenges that need to be met with this technology are salt handling and environmentally friendly recycle operations.

The step of scavenging an acidic by-product with a base is well known. Tertiary amines are commonly used, among these triethylamine is cited most often in the patent literature. Triethylamine is the least costly tertiary amine, but its most economical use requires a filtration step. A stoichiometric amount of triethylamine hydrochloride must be separated from the product. This is a mechanically intense unit operation and usually leads to poor yields if the product in the filter cake is not recovered. Either way, in addition to the already costly filtration or centrifugation step, additional costs relating to the disposal or further processing of the filter cake are added. Moreover, trialkylamine hydrochlorides are difficult to filter and typically require special 0.1 to 0.01 µm pressure filters.

Alternatively, the mercaptosilane can be reacted with an acid chloride in the absence of any amine. In this case, mixed chloroethoxysilanes are formed by relatively fast side reactions. Theoretically, the formation of these chloroethoxysilanes can be prevented by efficient removal of HCl. However, due to its covalent nature, anhydrous hydrogen chloride has a significant solubility in almost any non-polar organic medium and turns out to be very difficult to remove. In fact, almost any binary system containing HCl behaves in a highly non-ideal manner. Prior art includes specially designed contactors, e.g. a falling film reactor, a Couette reactor, a rotating disk contactor, etc., that are designed to facilitate removal of a gaseous species. However, efficient removal of highly reactive species is very difficult. In the case of HCl removal it may not be facilitated to a level where transesterification to chloroethoxysilanes is low enough to obtain a product that contains only trace amounts of these molecules.

It is possible, although technically difficult, to neutralize chloroethoxysilanes with neutralizing agents. The highly reactive thiocarboxylate group enhances this difficulty, particularly when basic inorganic neutralizing agents are used.

Another alternative technology is to react mercaptosilanes with alkali metals to yield the alkali organothiolates prior to the main reaction with the acid chloride. Hence, neutral sodium chloride is being formed as by-product.

The concept of scavenging a highly reactive acidic by-product like anhydrous hydrogen chloride with a tertiary amine is generally known as a synthesis technique.

U.S. Pat. No. 6,229,036 B1 describes the amine-assisted addition of a chlorosilane to a mercapto silane to produce sulfanylsilanes. Triethylamine is explicitly mentioned in the examples. Removal of the corresponding amine hydrochloride salt is achieved by filtration. The amine hydrochloride salt cannot be separated by a water/brine wash since silyl-blocked mercaptans hydrolyze in water. For example, U.S. Pat. No. 6,147,242 describes the preparation of silylalkylthiols by reacting silylalkylsulfanylsilanes with water. Hence, it is demonstrated that the Si—S bond is hydrolyzed faster than Si—OEt bonds.

U.S. 2001/00556139 B1 and EP 1 142 896 A1 describe the reaction between triazine compounds containing functional groups (e.g. chlorine) and mercaptosilanes to yield sulfur silane-triazine derivatives. A relevant example is included: The amine (triethylamine) assisted addition of mercaptopropyltriethoxysilane to cyanuric chloride (2,4,6-trichloro-1,3,5-triazine). Separation of the triethylamine hydrochloride salt from the product (1,3,5-tris(mercaptopropyltriethoxysilyl) triazine) is achieved through filtration. Triethylamine is the only amine that is explicitly mentioned.

U.S. Pat. No. 6,414,061 B1 describes novel blocked mercaptosilanes and includes methods of preparation. In Example 9 of the patent, the preparation of 3-(octanoylthio)-1-propyltriethoxysilane is described using triethylamine as the acid scavenger. Separation of triethylamine hydrochloride from the product was achieved through filtration (two times: first through a 0.1 µm filter, and then through a 0.01 µm filter).

The use of an aqueous phase in the production of polysulfidic silanes, such as bis(triethoxysilylpropyl) tetrasulfide and the corresponding disulfide, two articles of commerce, is prior art. The aqueous phase can be present during the reaction (phase transfer catalyzed reaction of chloropropyltriethoxysilane with water soluble $M_2S_n$ and/or MSH and/or elemental sulfur (M is ammonium or alkali metal) or can be introduced after completion of reaction to separate the product from the reaction mixture.

U.S. Pat. No. 5,405,985 describes the manufacture of molecules of the formula $Z-Alk-S_n-Alk-Z$. A compound of the formula Z-Alk-X, e.g. chloropropyltriethoxysilane, is reacted with ammonium or alkali polysulfide in the presence of an aqueous phase and a phase transfer catalyst. The by-product of the reaction, ammonium or alkali halide, most commonly sodium chloride, stays in the aqueous phase after completion of reaction.

U.S. Pat. No. 6,294,683 B1 describes the preparation of sulfur-containing organosilicon compounds by reacting aqueous solutions of various polysulfidic anions in saturated sodium chloride brine solutions with chloropropyltriethoxysilane (CPTES) supported on carbon black in the presence of a phase transfer catalyst.

U.S. Pat. No. 6,384,255 B1 describes the preparation of molecules of the formula Z-Alk-$S_n$-Alk-Z by phase transfer catalysis techniques. The phase transfer catalyst, elemental sulfur, and sulfide compounds of the formula $M_2S_n$ or MHS (M is ammonium or an alkali metal) are mixed in water and allowed to react to an intermediate reaction product. In a second step, this intermediate reaction product is reacted with an organosilane, preferably chloropropyltriethoxysilane (CPTES). The process requires a filtration step to remove residual sulfides from the organic phase.

U.S. Pat. No. 6,384,256 B1 differs from U.S. Pat. No. 6,384,255 B1 in the sense that in the first reaction step, an alkali metal hydroxide compound is reacted with a sulfide compound of the formula $M_2S_n$ or MHS (M is ammonium or an alkali metal), and elemental sulfur in water to form a polysulfide mixture which is then reacted with CPTES in the presence of a phase transfer catalyst. The pH of the aqueous phase is adjusted using a buffer. According to the patent, this process minimizes or eliminates hydrogen sulfide as a side product. It requires a filtration step to remove residual sulfides from the organic phase.

In U.S. Pat. No. 6,448,426 B1, a very similar reaction is described as in U.S. Pat. No. 6,384,255 B1. This patent also addresses the separation of the sulfur-containing organosilicon compounds from the product mixture by adding water or a dilute acidic solution to the product mixture, and phase separating the product mixture into an organic phase that contains the product and into an aqueous phase that contains ionic polysulfides.

SUMMARY OF THE INVENTION

In accordance with the invention a process for making a blocked mercaptosilane is provided, comprising the steps of:
reacting mercaptosilane with organic or inorganic halide or anhydride in the presence of at least one acid acceptor to produce a slurry reaction product, wherein said acid acceptor in free form is substantially water insoluble and the respective salts of said acid acceptor are substantially water soluble;
washing the slurry reaction product with water or brine (hereinafter referred to as "water/brine wash") to produce an organic phase that comprises the blocked mercaptosilane and an aqueous phase that is immiscible with the organic phase and that comprises the respective salt of the acid acceptor.

Recycle of the acid acceptor is achieved by adding base (e.g., caustic) to the aqueous phase to yield free acid acceptor which can be reused in the process.

The acid acceptor, preferably trialkylamine and in particular tri-n-propylamine (TNPA), that is used in this process is substantially water insoluble. The material reacts very rapidly with HCl to form the corresponding hydrochloride salt that, on the other hand, has very high solubility in aqueous phases. These properties become very attractive when a water/brine wash step is employed in the process to separate the amine hydrochloride from the product phase. The discharged aqueous phase from the process does not require additional treatment before disposal. The only limitation in this process is the rate of hydrolysis of the silane in the presence of water and a base. The rate of hydrolysis can be slowed down by temperature control. The use of a water/brine wash to purify an organosilane runs counter to common practice, and, at first glance, appears to be in contradiction to the high reactivity of most organosilanes with water. It may also be desirable to employ an acid acceptor in which water exhibits little or no solubility, i.e., less than about 0.2% and more preferably less than 0.15% solubility so that subsequent drying operations are unnecessary. Since the solubility of water in tri-n-propylamine is very low (about 0.12%), tri-n-propylamine represents a particularly good choice of acid acceptor from this vantage point.

To recover the acid acceptor, base, e.g., caustic solution (the least expensive base on the market), can be used to wash the aqueous phase to yield free acid acceptor and sodium chloride. The free acid acceptor, preferably trialkylamines and in particular tri-n-propylarnine, will phase separate from the aqueous phase and can be recycled to the process.

Use of an excess amount of acid acceptor, e.g. at least 10% molar excess, may be desirable in order to assure complete HCl scavenging towards the end of the reaction. This excess material needs to be separated from the product in a stripping process. Hence, the acid acceptor advantageously should not have a too high a boiling point. Higher tertiary alkylamines, of particular interest would be tri-n-butylamine (TNBA), have slightly better solubility characteristics than TNPA. However, their significantly higher boiling point (216° C. vs. 156° C. of TNPA) renders the removal of the excess portion economically less feasible.

With this technology it is possible to manufacture thiocarboxylic silanes from mercaptosilanes and acid chlorides in high purity without the need of filtering stoichiometric equivalents of salt. Separating large amounts of salts by filtration or centrifugation is a mechanically intense unit operation with frequently occurring maintenance events. The extraction of salt by an aqueous phase is favored over a filtration step on a large scale, but becomes even more advantageous when the process is run in continuous mode where a combination of static mixer (low cost and almost maintenance free operation) and decanter can be used to mix and settle the phases.

The new technology offers a cost efficient and environmentally friendly way to manufacture sulfur-containing organosilicon compounds, in particular thiocarboxylic silanes. These compounds have been identified as suitable coupling agents in the rubber compounding industry. The combination of using a suitable acid scavenger and performing a water/brine wash opens the door to continuous operation of the entire process, including recycle operations that are necessary to recover the acid scavenger. The process does not contain maintenance intense unit operations, such as filtration or centrifugation steps. The potential for continuous processing of sulfur silanes, which have grown to commodity scale in a highly competitive market over the last decade, provides a route to significant cost savings of these otherwise fairly expensive compounds.

DETAILED DESCRIPTION OF THE INVENTION

The invention is the combination of using a water-insoluble or almost water-insoluble acid acceptor, preferably a trialkylamine and in particular tri-n-propylamine, with a subsequent water/brine wash step to separate the product from the solid by-product, e.g., tri-n-propylamine hydrochloride. The solubility of the acid acceptor in aqueous phases is extremely important for efficiency and cost of the recycle operations. The solubility is extremely low in aqueous phases with high ionic strength. Solubility values for triethylamine, tri-n-propylamine, and tri-n-butylamine are shown in Table 1 (Method: Gas chromatography, sample preparation by extraction with hexane).

The data in Table 1 also show that TNPA and TNBA have much lower solubility in water than TEA. In addition, the solubility characteristics of TNPA and TNBA are not widely different. Interestingly, the solubility of TNBA in aqueous phases does not appear to depend largely on the ionic strength of the solution. In the literature, the solubility values of TEA in water commonly range from 3.0 to 5.5%. Below 18.7° C., TEA is classified as completely miscible. TNPA is classified as very slightly soluble and TNBA as insoluble.

TABLE 1

Solubility of different tri-n-alkylamines in various aqueous phases.

| Composition of aqueous phase | TEA, ppm | TNPA, ppm | TNBA, ppm |
|---|---|---|---|
| Aqueous phase: De-ionized water | 55,234 | 409 | 235 |
| Aqueous phase: 20% NaCl solution | 5,874 | 164 | 297 |
| Aqueous phase: 20% NaCl + 5% NaOH solution | 770 | 84 | 214 |
| Aqueous decant phase after TPA recovery | — | 57 | — |
| Replicate | — | 61 | — |
| Replicate | — | 60 | — |

The trend of the three synthetic solutions indicates that the amine concentrations are the highest in de-ionized water. In 20% sodium chloride solution the levels are significantly reduced. The lowest amine levels are observed in the combined solution containing 20% NaCl and 5% NaOH. This composition is closest to the aqueous phase after amine extraction.

Another significant property is the solubility of water in the amine. At 25° C., the solubility of water in triethylamine is approximately 10%, while the solubility of water in tri-n-propylamine is 0.12%. Hence, the recycle of triethylamine involves expensive drying operations. In the case of TNPA, it is much easier and less expensive to remove the low water content, which could even be tolerated in the process eliminating drying operations altogether.

Hence, with tri-n-propylamine it is possible to perform an economical recycle of the process streams and minimize waste disposal cost. TNPA can also be recycled if the process uses a filtration/centrifugation step instead of a water/brine wash. However, a water/brine wash is preferred over conventional filtration/centrifugation operations because (a) amine hydrochloride salts are highly soluble in aqueous phase and are essentially quantitatively extracted, (b) filtration/centrifugation techniques are maintenance intense and show high failure rates, (c) no product is lost or needs to be recovered from the phase that contains the amine hydrochloride, and (d) drying operations of recycle streams are less expensive or may even completely be avoided.

Comparing solubility characteristics (amine in water and water in amine), and also taking boiling point, molar weight, and cost into account, tri-n-propylamine is the optimum choice of amine.

The combination of using a water-insoluble or almost water-insoluble acid acceptor in combination with a water/brine wash is novel. This novel process opens up an economically feasible way for the manufacture of blocked mercaptosilanes. Organic or inorganic halides or anhydrides, preferably chlorides, can be reacted with mercaptosilanes, most preferably mercaptopropyltriethoxysilane, in the presence of an acid acceptor that has a very low solubility in aqueous phases, yet forms a highly soluble salt with the respective acid, e.g. anhydrous hydrogen chloride or carboxylic acid.

Suitable organic halides or anhydrides include but are not limited to acid halides (e.g. propionyl, hexanoyl, 2-ethylhexanoyl, octanoyl, lauroyl, or oleoyl), alkyl halides, alkenyl halides, aryl halides, and aralkyl halides, and carboxylic anhydrides (e.g. acetic, propionic, hexanoic, 2-ethylhexanoic, octanoic, lauric, and oleic).

Suitable inorganic halides or anhydrides include but are not limited to thionyl halide, sulfuryl halide, alkyl, or alkenyl, or aryl, or aralkyl sulfonic halides or anhydrides, and alkyl, or alkenyl, or aryl, or aralkyl phosphorus oxy halides.

As used herein, halide includes chloride, bromide, and iodide, most preferably chloride, alkyl includes straight, branched, and cyclic alkyl groups, and alkenyl includes straight, branched, and cyclic alkenyl groups containing one or more carbon-carbon double bonds. Specific alkyls include methyl, ethyl, propyl, isobutyl, and specific aryl and aralkyls include phenyl, tolyl, and phenethyl. As used herein, acyclic alkenyl or acyclic alkenyl also includes bicyclic and higher cyclic structures, as well as cyclic structures further substituted with alkyl groups. Representative examples include norbornyl, norbornenyl, ethylnorbornyl, ethylnorbornenyl, ethylcyclohexyl, ethylcyclohexenyl, and cyclohexylcyclohexyl.

Mercaptosilanes include those corresponding to the general formula:

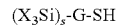

$(X_3Si)_s$-G-SH wherein X is independently selected from the group consisting of —Cl, —Br, RO—, RC(=O)O—, $R_2C$=NO—, $R_2$NO— or $R_2$N—, —R, —$(OSiR_2)_t(OSiR_3)$ wherein each R is chosen independently from hydrogen, straight, cyclic, or branched alkyl that may or may not contain unsaturation, alkenyl groups, aryl groups, and aralkyl groups, with each R containing from 1 to 18 carbon atoms, and at least one X is not —R; G is a monovalent or polyvalent group derived by substitution of alkyl, alkenyl, aryl, or aralkyl wherein G can contain from 1 to 18 carbon atoms, and s is 1 to 3.

The blocked mercaptosilanes produced by the process of the invention can be represented by the Formulae (1–2):

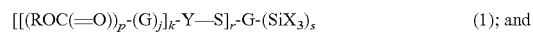

$[[(ROC(=O))_p\text{-}(G)_j]_k\text{-}Y\text{-}S]_r\text{-}G\text{-}(SiX_3)_s$ (1); and

$[X_3Si]_q\text{-}G]_a\text{-}[Y\text{-}[S\text{-}G\text{-}SiX_3]_b]_c$ (2)

wherein

Y is a polyvalent species $(Q)_zA(=E)$, preferably selected from the group consisting of —C(=NR)—; —SC(=NR)—; —SC(=O)—; (—NR)C(=O)—; (—NR)C(=S)—; —OC(=O)—; —OC(=S)—; —C(=O)—; —SC(=S)—; —C(=S)—; —S(=O)—; —S(=O)$_2$—; —OS(=O)$_2$—; (—NR)S(=O)$_2$—; —SS(=O)—; —OS(=O)—; (—NR)S(=O)—; —SS(=O)$_2$—; (—S)$_2$P(=O)—; —(—S)P(=O)—; —P(=O)(-)$_2$; (—S)$_2$P(=S)—; —(—S)P(=S)—; —P(=S)(-)$_2$; (—NR)$_2$P(=O)—; (—NR)(—S)P(=O)—; (—O)(—NR)P(=O)—; (—O)(—S)P(=O)—; (—O)$_2$P(=O)—; —(—O)P(=O)—; (—NR)P(=O)—; (—NR)$_2$P(=S)—; (—NR)(—S)P(=S)—; (—O)(—NR)P(=S)—; (—O)(—S)P(=S)—; (—O)$_2$P(=S)—; —(—O)P(=S)—; and —(—NR)P(=S)—; each wherein the atom (A) attached to the unsaturated heteroatom (E) is attached to the sulfur, which in turn is linked via a group G to the silicon atom;

each R is chosen independently from hydrogen, straight, cyclic, or branched alkyl that may or may not contain unsaturation, alkenyl groups, aryl groups, and aralkyl groups, with each R containing from 1 to 18 carbon atoms; each G is independently a monovalent or polyvalent group derived by substitution of alkyl, alkenyl, aryl, or aralkyl wherein G can contain from 1 to 18 carbon atoms, and if G directly bonded to Y is univalent (i.e., if p=0), G can be a hydrogen atom;

X is independently selected from the group consisting of —Cl, —Br, RO—, RC(=O)O—, $R_2$C=NO—, $R_2$NO— or $R_2$N—, —R, —(OSi$R_2$)$_t$(OSi$R_3$) wherein each R and G is as above and at least one X is not —R;

Q is oxygen, sulfur, or (—NR—);

A is carbon, sulfur, phosphorus, or sulfonyl;

E is oxygen, sulfur, or NR;

p is 0 to 5; r is 1 to 3; z is 0 to 2; q is 0 to 6; a is 0 to 7; bis 1 to 3; j is 0 to 1, but it may be 0 only if p is 1; c is 1 to 6, preferablyl to 4; t is to 5; s is 1 to 3; k is 1 to 2; with the provisos that (A) if A is carbon, sulfur, or sulfonyl, then (i) a+b=2 and (ii) k=1; (B) if A is phosphorus, then a+b=3 unless both (i) c>1 and (ii) b=1, in which case a=c+1; and (C) if A is phosphorus, then k is 2.

Representative examples of the functional groups (—YS—) present in the silanes of the present invention include thiocarboxylate ester, —C(=O)S— (any silane with this functional group is a thiocarboxylate ester silane); dithiocarboxylate, —C(=S)S— (any silane with this functional group is a dithiocarboxylate ester silane); thiocarbonate ester, —O—C(=O)S— (any silane with this functional group is a thiocarbonate ester silane); dithiocarbonate ester, —S—C(=O)S— and —O—C(=S)S— (any silane with this functional groups is a dithiocarbonate ester silane); trithiocarbonate ester, —S—C(=S)S— (any silane with this functional group is a trithiocarbonate ester silane); dithiocarbamate ester, (—N—)C(=S)S— (any silane with this functional group is a dithiocarbamate ester silane); thiosulfonate ester, —S(=O)$_2$S— (any silane with this functional group is a thiosulfonate ester silane); thiosulfate ester, —O—S(=O)$_2$S— (any silane with this functional group is a thiosulfate ester silane); thiosulfamate ester, (—N—)S(=O)$_2$S— (any silane with this functional group is a thiosulfamate ester silane); thiosulfinate ester, —S(=O)S— (any silane with this functional group is a thiosulfinate ester silane); thiosulfite ester, —O—S(=O)S— (any silane with this functional group is a thiosulfite ester silane); thiosulfimate ester, (—N—)S(=O)—S— (any silane with this functional group is a thiosulfimate ester silane); thiophosphate ester, P(=O)(O—)$_2$(S—) (any silane with this functional group is a thiophosphate ester silane); dithiophosphate ester, P(=O)(O—)(S—)$_2$ or P(=S)(O—)$_2$(S—) (any silane with this functional group is a dithiophosphate ester silane); trithiophosphate ester, P(=O)(S—)$_3$ or P(=S)(O—)(S—)$_2$ (any silane with this functional group is a trithiophosphate ester silane); tetrathiophosphate ester P(=S)(S—)$_3$ (any silane with this functional group is a tetrathiophosphate ester silane); thiophosphamate ester, —P(=O)(—N—)(S—) (any silane with this functional group is a thiophosphamate ester silane); dithiophosphamate ester, —P(=S)(—N—)(S—) (any silane with this functional group is a dithiophosphamate ester silane); thiophosphoramidate ester, (—N—)P(=O)(O—)(S—) (any silane with this functional group is a thiophosphoramidate ester silane); dithiophosphoramidate ester, (—N—)P(=O)(S—)$_2$ or (—N—)P(=S)(O—)(S—) (any silane with this functional group is a dithiophosphoramidate ester silane); trithiophosphoramidate ester, (—N—)P(=S)(S—)$_2$ (any silane with this functional group is a trithiophosphoramidate ester silane).

Novel silanes of the present invention are those wherein Y groups are —C(=NR)—; —SC(=NR)—; —SC(=O)—; —OC(=O)—; —S(=O)—; —S(=O)$_2$—; —OS(=O)$_2$—; —(NR)S(=O)$_2$—; —SS(=O)—; —OS(=O)—; —(NR)S(=O)—; —SS(=O)$_2$—; (—S)$_2$P(=O)—; —(—S)P(=O)—; —P(=O)(-)$_2$; (—S)$_2$P(=S)—; —(—S)P(=S)—; —P(=S)(-)$_2$; (—NR)$_2$P(=O)—; (—NR)(—S)P(=O)—; (—O)(—NR)P(=O)—; (—O)(—S)P(=O)—; (—O)$_2$P(=O)—; —(—O)P(=O)—; —(—NR)P(=O)—; (—NR)$_2$P(=S)—; (—NR)(—S)P(=S)—; (—O)(—NR)P(=S)—; (—O)(—S)P(=S)—; (—O)$_2$P(=S)—; —(—O)P(=S)—; and —(—NR)P(=S)—. Particularly preferred of these are —OC(=O)—; —SC(=O)—; —S(=O)—; —OS(=O)—; —(—S)P(=O)—; and —P(=O)(-)$_2$.

A preferred silane would be one wherein Y is —C(=O)— wherein G has a primary carbon attached to the carbonyl and is a $C_2$–$C_{12}$ alkyl, more preferably a $C_6$–$C_8$ alkyl.

Another preferred structure is of the form $X_3$SiGSC(=O)GC(=O)SGSi$X_3$ wherein G is a divalent hydrocarbon.

Examples of G include —(CH$_2$)n— wherein n is 1 to 12, diethylene cyclohexane, 1,2,4-triethylene cyclohexane, and diethylene benzene. It is preferred that the sum of the carbon atoms within the G groups within the molecule are from 3 to 18, more preferably 6 to 14. This amount of carbon in the blocked mercaptosilane facilitates the dispersion of the inorganic filler into the organic polymers, thereby improving the balance of properties in the cured filled rubber.

Preferable R groups are alkyls of $C_1$ to $C_4$ and H.

Specific examples of X are methoxy, ethoxy, isobutoxy, propoxy, isopropoxy, acetoxy, and oximato. Methoxy, acetoxy, and ethoxy are preferred. At least one X must be reactive (i.e., hydrolyzable).

Preferred embodiments are wherein p is 0 to 2; X is RO— or RC(=O)O—; R is hydrogen, phenyl, isopropyl, cyclohexyl, or isobutyl; G is a substituted phenyl or substituted straight chain alkyl of $C_2$ to $C_{12}$. The most preferred embodiments include those wherein p is zero, X is ethoxy, and G is a $C_3$–$C_{12}$ alkyl derivative.

Representative examples of the silanes which can be produced according to the process of the present invention include: 2-triethoxysilyl-1-ethyl thioacetate; 2-trimethoxysilyl-1-ethyl thioacetate; 2-(methyldimethoxysilyl)-1-ethyl thioacetate; 3-trimethoxysilyl-1-propyl thioacetate; triethoxysilylmethyl thioacetate; trimethoxysilylmethyl thioacetate; triisopropoxysilylmethyl thioacetate; methyldiethoxysilylmethyl thioacetate; methyldimethoxysilylmethyl thioacetate; methyldiisopropoxysilylmethyl thioacetate; dimethylethoxysilylmethyl thioacetate; dimethylmethoxysilylmethyl thioacetate; dimethylisopropoxysilylmethyl thioacetate; 2-triisopropoxysilyl-1-ethyl thioacetate; 2-(methyldiethoxysilyl)-1-ethyl thioacetate; 2-(methyldiisopropoxysilyl)-1-ethyl thioacetate; 2-(dimethylethoxysilyl)-1-ethyl thioacetate; 2-(dimethylmethoxysilyl)-1-ethyl thioacetate; 2-(dimethylisopropoxysilyl)-1-ethyl thioacetate; 3-triethoxysilyl-1-propyl thioacetate; 3-triisopropoxysilyl-1-propyl thioacetate; 3-methyldiethoxysilyl-1-propyl thioacetate; 3-methyldimethoxysilyl-1-propyl thioacetate; 3-methyldiisopropoxysilyl-1-propyl thioacetate; 1-(2-triethoxysilyl-1-ethyl)-4-thioacetylcyclohexane; 1-(2-triethoxysilyl-1-ethyl)-3-thioacetylcyclohexane; 2-triethoxysilyl-5-thioacetylnorbornene; 2-triethoxysilyl-4-thioacetylnorbornene; 2-(2-triethoxysilyl-1-ethyl)-5-thioacetylnorbornene; 2-(2-triethoxysilyl-1-ethyl)-4-thioacetylnorbornene; 1-(1-oxo-2-thia-5- triethoxysilylpenyl)benzoic acid; 6-triethoxysilyl-1-hexyl thioacetate; 1-triethoxysilyl-5-hexyl thioacetate; 8-triethoxysilyl-1-octyl thioacetate; 1-triethoxysilyl-7-octyl thioacetate; 6-triethoxysilyl-1-hexyl thioacetate; 1-triethoxysilyl-5-octyl thioacetate; 8-trimethoxysilyl-1-octyl thioacetate;1-trimethoxysilyl-7-octyl thioacetate; 10-triethoxysilyl-1-decyl thioacetate; 1-triethoxysilyl-9-decyl thioacetate; 1-triethoxysilyl-2-butyl thioacetate; 1-triethoxysilyl-3-butyl thioacetate; 1-triethoxysilyl-3-methyl-2-butyl thioacetate; 1-triethoxysilyl-3-methyl-3-butyl thioacetate; 3-trimethoxysilyl-1-propyl thiooctanoate; 3-triethoxysilyl-1-propyl thiopalmitate; 3-triethoxysilyl-1-propyl thiooctanoate; 3-triethoxysilyl-1-propyl thiobenzoate; 3-triethoxysilyl-1-propyl thio-2-ethylhexanoate; 3-methyldiacetoxysilyl-1-propyl thioacetate; 3-triacetoxysilyl-1-propyl thioacetate; 2-methyl-diacetoxysilyl-1-ethyl thioacetate; 2-triacetoxysilyl-1-ethyl thioacetate; 1-methyldiacetoxysilyl-1-ethyl thioacetate; 1-triacetoxysilyl-1-ethyl thioacetate; tris-(3-triethoxysilyl-1-propyl)trithiophosphate; bis-(3-triethoxysilyl-1-propyl)methyldithiophosphonate; bis-(3-triethoxysilyl-1-propyl)ethyldithiophosphonate; 3-triethoxysilyl-1-propyldimethylthiophosphinate; 3-triethoxysilyl-1-propyldiethylthiophosphinate; tris-(3-triethoxysilyl-1-propyl)tetrathiophosphate; bis-(3-triethoxysilyl-1-propyl) methyltrithiophosphonate; bis-(3-triethoxysilyl-1-propyl) ethyltrithiophosphonate; 3-triethoxysilyl-1-propyldimethyldithiophosphinate; 3-triethoxysilyl-1-propyldiethyldithiophosphinate; tris-(3-methyldimethoxysilyl-1-propyl)trithiophosphate; bis-(3-methyldimethoxysilyl-1-propyl)methyldithiophosphonate; bis-(3-methyldimethoxysilyl-1-propyl)ethyldithiophosphonate; 3-methyldimethoxysilyl-1-propyldimethylthiophosphinate; 3-methyldimethoxysilyl-1-propyldiethylthiophosphinate; 3-triethoxysilyl-1-propylmethylthiosulphate; 3-triethoxysilyl-1-propylmethanethiosulphonate; 3-triethoxysilyl-1-propylethanethiosulphonate; 3-triethoxysilyl-1-propylbenzenethiosulphonate; 3-triethoxysilyl-1-propyltoluenethiosulphonate; 3-triethoxysilyl-1-propylnaphthalenethiosulphonate; 3-triethoxysilyl-1-propylxylenethiosulphonate; triethoxysilylmethylmethylthiosulphate; triethoxysilylmethylmethanethiosulphonate; triethoxysilylmethylethanethiosulphonate; triethoxysilylmethylbenzenethiosulphonate; triethoxysilylmethyltoluenethiosulphonate; triethoxysilylmethylnaphthalenethiosulphonate; and triethoxysilylmethylxylenethiosulphonate.

It is understood that the partial hydrolyzates of these blocked mercaptosilanes (i.e., blocked mercaptosiloxanes) may also be encompassed by the blocked mercaptosilanes herein, in that these partial hydrolyzates may be a side product of manufacture of the blocked mercaptosilane.

In principle, any acid acceptor (base) can be used to scavenge the acidic by-product. The required properties for this acid acceptor are (a) to not hydrolyze with the product, (b) to not react with the reactive organic or inorganic halide or anhydride, and (c) to have sufficient solubility in organic media or the ability to be carried into organic media. Inorganic bases like alkali or alkaline earth carbonates and alkali or alkaline earth phosphates can be employed, optionally in the presence of a phase transfer catalyst, e.g. tetralkylammonium or -phosphonium halides. Tertiary amines or phosphines are undoubtedly the most practical choice. Any tertiary amine or phosphine with the above-mentioned solubility characteristics can be used successfully to run this process. The amines are more favorable choices than the corresponding phosphines due to their much lower cost. Examples for suitable acid acceptors include but are not limited to tri-n-alkylamines or -phosphines, branched trialkylamines or phosphines, aromatic amines or phosphines, e.g. pyridine, quinoline, isoquinoline, dialkylanilines or phosphines, in particular dimethylaniline and dimethylphenylphosphine, and also cyclic non-aromatic amines, e.g. triethylenediamine (also referred to as 1.4-diazabicyclo[2.2.2]octane) or hexamethylenetetramine.

This method is restricted only by the rate of hydrolysis that an organosilane may have at or below ambient temperature in the presence of an aqueous phase. For example, instead of an acid halide, any reactive organic or inorganic halide could be used in this process as long as the product does not react with water.

Tri-n-propylamine has been identified as a very suitable acid acceptor, because of (a) its low solubility in aqueous phases, in particular in those with high ionic strength, (b) its desirable boiling point, (c) its commercial availability at relatively low cost, and (d) its good biodegradability.

The uniqueness of this process is the combination of using the above-mentioned acid acceptor with a key unit operation, namely a water or brine wash, to separate the solid by-product, tri-n-propylamine hydrochloride, from the product phase. The amount of water or brine needed for separating the hydrochloride salt from the organic phase is comparably small due to the very high solubility of amine hydrochlorides in aqueous phases.

Illustrative examples of the invention include the synthesis of thiocarboxylate-functional silanes from mercaptopropyltriethoxysilane with tri-n-alkylamines as acid acceptors and acid chlorides as electrophiles (Examples 1–11), and the synthesis of a thiophosphonyl-functional silane (Example 12). Example 13 illustrates the synthetic procedure of a thiocarboxylate-functional silane by using an anhydride instead of an acid chloride. In Examples 14–16, the invention is illustrated with aromatic and branched aliphatic amines as acid acceptors. Example 17 illustrates that the water wash step can also be used in the synthesis of trimethoxy-functional silanes. Examples 1–17 are all in batch mode. In Example 18, the concept of using an acid acceptor in combination with a water/brine wash is extended to the continuous mode. The reaction is carried out in a series of CSTR's (continuous stirred tank reactors).

A. Batch Operation

In this mode, the entire reaction (including water/brine wash, strip, and recycle) can be performed in one reactor. The procedure is described in detail for a laboratory scale experiment in Examples 1 and 2 (using TEA) and in Examples 3 (using TNPA). In the first two examples, the amine cannot quantitatively be recycled, in the third case the recycle operations are described in detail. Examples 4 and 5 illustrate that drying operations may be obsolete if TNPA is used as the acid acceptor. Octanoyl chloride was the limiting reagent in all experiments.

EXAMPLE 1

TEA Assisted Reaction With Water/brine Wash.

At ambient temperature, 2492g (10.45 moles) mercaptopropyltriethoxysilane (MPTES), 1058 g (10.45 moles) TEA, 3390 ml isooctane, and 40 ml toluene (to simulate residual clean-up toluene in a production scale reactor) were added to a 12-L 4-neck RBF equipped with mechanical stirrer, dry ice condenser, $N_2$ inlet & thermocouple, and addition funnel. MPTES and TEA were mixed with the solvent and 1545 g (9.50 moles) of octanoyl chloride were slowly added over a period of 40 minutes through the addition funnel. The temperature increased from 22° C. to 65° C. during the addition with no additional cooling. The flask was allowed to cool overnight. An aqueous 10% NaCl solution was prepared and 1267 g of this solution were added to the flask. The contents were agitated for 5 minutes and then allowed to settle for 15 minutes. The organic phase was separated from the aqueous phase and dried with 5.0 g anhydrous magnesium sulfate (15 minutes with agitation). The material was filtered through a 1-micron filter pad in a pressure filter. The product was stripped at 50 mm Hg and heated to 130° C. where it was held at for 30 minutes. Finally, the product was allowed to cool and then polish filtered. Recovered 3440.9 g of 3-octanoyl-1-thiopropyltriethoxysilane as a clear, pale yellow liquid that contained 90.4% 3-octanoyl-1-thiopropyltriethoxysilane, 3.1% MPTES, and some heavies. The decanted aqueous phase had a strong amine odor and was disposed.

EXAMPLE 2

TEA Assisted Reaction with Water/brine Wash and Amine Recovery

At ambient temperature, 396.3 g (1.66 moles) MPTES, 176.2 g (1.74 moles) TEA, and 655 ml isooctane were added to a 2-L 4-neck round bottom flask with bottom take-off equipped with mechanical stirrer, dry ice condenser, $N_2$ inlet & thermocouple, and addition funnel. MPTES and TEA were mixed with the solvent and 257.5 g (1.58 moles) of octanoyl chloride were added slowly over a period of 40 minutes through the addition funnel. During the addition, the temperature increased from ambient to 86.5° C. The slurry was water washed at 31° C. with 212 g 10% NaCl solution. After having settled for 15 minutes, the aqueous phase was decanted. The organic layer was dried with 5 g magnesium sulfate (15 minutes agitation), filtered, and returned to the flask. The solution was stripped at 50–80 mm Hg while heating to 130° C. Recovered 547.0 g of 3-octanoyl-1-thiopropyltriethoxysilane as a clear, pale yellow liquid that contained 94.7% pure material, 1.5% MPTES and some heavies. The amine phase was recovered by adding 20% NaOH solution to the aqueous phase. After mixing, the bottom layer was decanted. Recovered 165.3 g amine phase with purity of 93.9% (97.0% recovery). The aqueous salt solution still exhibited a strong amine odor.

EXAMPLE 3

TNPA Assisted Reaction Series with Water/brine Wash and Multiple Amine & Solvent Recoveries and Drying Operations STAGE 1: At ambient temperature, 396.3 g (1.66 moles) MPTES, 249.7 g (1.74 moles) tri-n-propylamine (TNPA), and 475 g petroleum ether (VM&P naphtha) were added to a 2-L 4-neck round bottom flask with bottom take-off equipped with mechanical stirrer, dry ice condenser, $N_2$ inlet & thermocouple, and addition funnel. MPTES and TNPA were mixed with the solvent and 257.5 g (1.58 moles) of octanoyl chloride were added slowly through the addition funnel. The temperature increased from ambient to 60° C. during the addition. The slurry was water washed with 204 g 10% NaCl solution (5 min. stirring, 15 min. settling). The aqueous phase (529.8 g) was decanted and the organic phase dried with 5.0 g anhydrous magnesium sulfate. The solution was filtered through a 1-micron filter pad. The material was vacuum stripped at 45–50 mm Hg. The temperature was increased very slowly to 130° C. and held for one hour. Recovered 346.5 g of lights that were later dried with magnesium sulfate and filtered. Recovered 465.9 g of stripped material as a pale yellow liquid that was subsequently polish filtered. The stripped material contained 92.0% 3-octanoyl-1-thiopropyl-triethoxysilane and also contained 3.5% MPTES and 1.0% heavies. The final yield was 74.4%. The lights contained 90.0% petroleum ether, 5.0% TNPA, 0.4% MPTES, and 0.1% product.

The amine phase was recovered by adding 350.0 g of 20% NaOH solution to the aqueous phase. After 15 minutes of mixing and 15 minutes of settling, the bottom layer was decanted. Recovered 263.5 g amine phase as a colorless, clear liquid. The recovered amine phase had a purity of 75.4% and also contained 10.0% product (hence the relatively low yield) and 0.1% MPTES (remainder was petroleum ether). The material contained 0.14% water and was dried with 5 g anhydrous magnesium sulfate (water content ~0% after drying).

STAGE 2: At ambient temperature, 396.3 g MPTES (1.66 moles), 231.5 g recycled amine phase containing 174.5 g (1.22 moles) TNPA, 58.7 g (0.41 moles) make-up TNPA, 329.3 g recycled solvent including 16.5 g (0.12 moles) excess amine from Stage 1, and 178.5 g make-up solvent were added to a 2-L 4-neck RBF with bottom take-off equipped with mechanical stirrer, dry ice condenser, $N_2$ inlet & thermocouple, and addition funnel. MPTES and TNPA were mixed with the solvent and 257.5 g (1.58 moles) of octanoyl chloride were added slowly through the addition funnel. The slurry was water washed with 200 g 10% NaCl solution (5 min. stirring, 15 min. settling). The aqueous phase (492.0 g) was decanted and the organic phase dried with 5.0 g anhydrous magnesium sulfate. The solution was filtered through a 1-micron filter pad. The material was vacuum stripped at 45–50 mm Hg. The temperature was increased very slowly to 130° C. and held for one hour. Recovered 417.0 g of lights and 519.4 g of stripped material as a pale yellow liquid that was subsequently polish filtered. The stripped material contained 96.2% 3-octanoyl-1-thiopropyltriethoxysilane and also contained 1.4% MPTES and 0.9% heavies. The final yield was 86.7%. The lights contained 88.0% petroleum ether, 5.2% TNPA, 1.1% MPTES, and 0.8% product.

The amine phase was recovered by adding 350.0 g of 20% NaOH solution to the aqueous phase. After 15 minutes of mixing and 15 minutes of settling, the bottom layer was decanted. The recovered amine phase had a purity of 87.6% and also contained 6.1% product and 5.9% petroleum ether. The material contained 0.02% water after drying.

Examples without any drying operations

The following two examples illustrate that the process can be run with tri-n-propylamine without the necessity of drying the recycled amine stream. In Example 4, TEA is used as the acid acceptor, in Example 5 the reaction is run with TNPA.

EXAMPLE 4

Recovery of TEA with Caustic Solution and Subsequent Use as an Acid Acceptor without Prior Drying TEA recovery: At ambient temperature, one liter of aqueous decant phase was combined with one liter of 20% caustic solution in a 3-L flask with bottom decant equipped with mechanical stirrer and nitrogen purge. The materials were agitated and then allowed to settle. The amine phase contained 2.95% water and the aqueous phase about 1500 ppm TEA (determined by headspace GC). This level of water is unacceptable and requires drying operations.

The experiment was repeated with 800 ml aqueous decant phase, 800 ml caustic solution and 400 ml isooctane. The recovered amine/isooctane phase contained 0.21% water and the aqueous phase about 1200 ppm TEA.

Main reaction: At ambient temperature, 396.3 g (1.66 moles) mercaptopropyltriethoxysilane (MPTES), 446.6 g TEA/isooctane (containing 176.4 g TEA (1.74 moles)), and 190 g additional isooctane were added to a 2-L 4-neck round bottom flask with bottom take-off equipped with mechanical stirrer, dry ice condenser, $N_2$ inlet & thermocouple, and addition funnel. MPTES and TNPA were mixed with the solvent and 257.5 g (1.58 moles) of octanoyl chloride were added slowly through the addition funnel. The slurry was water washed with 202.6 g 10% NaCl solution (5 min. stirring, 15 min. settling). The organic phase was hazy. The aqueous phase was decanted and the organic phase was dried with 5 g anhydrous magnesium sulfate. The drying agent was very clumpy and additional 5 g were added to the organic phase. The mixture was filtered and then vacuum stripped at 40 mm Hg. The temperature was increased very slowly to 130° C. (over a time span of 2 hrs.) and held for one hour. The stripped material contained 88.3% 3-octanoyl-1-thiopropyltriethoxysilane and also contained 6.5% MPTES and 2.3% heavies.

This example illustrates that it is possible to use TEA in combination with a water/brine wash. In principle, the drying operation of the recycled amine stream can be omitted if a non-polar organic solvent is added during the recovery step with caustic solution. However, even in this case, a significant amount of octanoyl chloride is converted to octanoic acid during the reaction. Consequently, the final product contains a high level of MPTES. Also, the addition of a non-polar solvent to the amine recovery operation poses technical difficulties, especially when performed in a continuous mode. In-addition, TEA levels of the aqueous waste stream are significantly higher than in the case of TNPA.

EXAMPLE 5

TNPA Assisted Reaction Series with Water/brine Wash and Multiple Amine & Solvent Recoveries and No Drying Operations STAGE 1: At ambient temperature, 396.3 g (1.66 moles) mercaptopropyltriethoxysilane (MPTES), 249.7 g (1.74 moles) tri-n-propylamine (TNPA), and 475 g petroleum ether (VM&P naphtha) were added to a 2-L 4-neck round bottom flask with bottom take-off equipped with mechanical stirrer, dry ice condenser, $N_2$ inlet & thermocouple, and addition funnel. MPTES and TNPA were mixed with the solvent and 257.5 g (1.58 moles) of octanoyl chloride were added slowly through the addition funnel. The slurry was water washed with 200 g 10% NaCl solution (5 min. stirring, 15 min. settling). The aqueous phase (511.0 g) was decanted. The material was vacuum stripped at 50 mm Hg. The temperature was increased very slowly to 130° C. (over a time span of 2 hrs.) and held for one hour. Recovered 485.6 g of lights and 526.7 g of stripped material as a pale yellow liquid that had been polish filtered through a 1-pm filter.

The stripped material contained 92.0% 3-octanoyl-1-thiopropyltriethoxysilane and also contained 3.8% MPTES and 0.8% heavies. The final yield was 84.0%. The lights contained 90.8% solvent, 4.7% TNPA, 0.4% MPTES, and 0.1% product. The water level was determined as 0.1 ppm.

The amine phase was recovered by adding 350.0 g of 20% NaOH solution to the aqueous phase. After 15 minutes of mixing and 15 minutes of settling, the bottom layer was decanted. Recovered 237.9 g amine phase as a colorless, clear liquid. The recovered amine phase had a purity of 94.1% and contained 2.8% product. The water level was 831 ppm.

STAGE 2: At ambient temperature, 396.3 g (1.66 moles) MPTES, 164.4 g recycled amine phase containing 159.5 g (1.11 moles) TNPA, 70 g (0.49 moles) make-up TNPA, 394.6 g recycled solvent including 19.4 g excess amine (0.14 moles), and 94.9 g make-up solvent were added to a 2-L 4-neck RBF with bottom take-off equipped with mechanical stirrer, dry ice condenser, $N_2$ inlet & thermocouple, and addition funnel. MPTES and TNPA were mixed with the solvent and 257.5 g (1.58 moles) of octanoyl chloride were added slowly through the addition funnel. The slurry was water washed with 200 g 10% NaCl solution (5 min. stirring, 15 min. settling). The aqueous phase (534.0 g) was decanted. The material was vacuum stripped at 50 mm Hg. The temperature was increased very slowly to 130° C. (over a time span of 2 hrs.) and held for one hour. Recovered 465.5 g of lights and 539.2 g of stripped material as a pale yellow liquid that had been polish filtered through a 1-μm filter. The stripped material contained 93.6% 3-octanoyl-1-thiopropyltriethoxysilane and also contained 1.9% MPTES and 2.3% heavies. The final yield was 87.6%. The lights contained 90.4% solvent, 3.4% TNPA, 1.0% MPTES, and 0.3% product.

The amine phase was recovered by adding 350.0 g of 20% NaOH solution to the aqueous phase. After 15 minutes of mixing and 15 minutes of settling, the bottom layer was decanted. Recovered 243.4 g amine phase as a colorless, clear liquid. The recovered amine phase had a purity of 85.0% and contained 6.7% product. The water level was 644 ppm.

This example illustrates that it is possible to run this reaction with recycled and non-dried streams if an amine is used that has very limited miscibility with water. Depending on the desired quality, a drying operation may still be incorporated into the reaction. Only a marginal increase in the heavies is observed when recycled streams are used without any drying. It is emphasized at this point that the cost for drying operations increases with the water level rendering TNPA much more economical than TEA.

Examples 6–17 illustrate additional reactions with various electrophiles and acid acceptors.

EXAMPLE 6

TNBA (tri-n-butylamine) Assisted Reaction Series Eith Water/brine Wash and Multiple Amine & Solvent Recoveries and No Drying Operations STAGE 1: At ambient temperature, 396.3 g (1.66 moles) mercaptopropyltriethoxysilane (MPTES), 322.5 g (1.74 moles) tri-n-butylamine (TNBA), and 475 g petroleum ether (VM&P naphtha) were added to a 2-L 4-neck round bottom flask with bottom take-off equipped with mechanical stirrer, dry ice condenser, $N_2$ inlet & thermocouple, and addition funnel. MPTES and TNBA were mixed with the solvent and 257.5 g (1.58 moles) of octanoyl chloride were added slowly through the addition funnel. The slurry was water washed with 200 g 10% NaCl solution (5 min. stirring, 15 min. settling). The aqueous phase (579.0 g) was decanted. The material was vacuum stripped at 50 mm Hg. The temperature was increased very slowly to 150° C. (over a time span of 2 hrs.) and held for one hour. Recovered 278.5 g of lights and 517.8 g of stripped material as a pale yellow liquid that had been polish filtered through a 1-μm filter.

The stripped material contained 96.4% 3-octanoyl-1-thiopropyltriethoxysilane and also contained 0.2% MPTES and 1.6% heavies. The final yield was 86.6%. The lights contained 85.8% solvent, 4.5% TNBA, 3.0% MPTES, and 1.9% product. The water level was determined as <0.1 ppm.

The amine phase was recovered by adding 350.0 g of 20% NaOH solution to the aqueous phase. After 15 minutes of mixing and 15 minutes of settling, the bottom layer was decanted. Recovered 306.0 g amine phase as a colorless, clear liquid. The recovered amine phase had a purity of 92.2% and contained 3.6% product. The water level was 434 ppm.

STAGE 2: At ambient temperature, 396.3 g (1.66 moles) MPTES, 275.9 g recycled amine phase containing 254.3 g (1.37 moles) TNBA, 57.6 g (0.31 moles) make-up TNBA, 236.5 g recycled solvent including 10.6 g excess amine (0.06 moles), and 261.6 g make-up solvent were added to a 2-L 4-neck RBF with bottom take-off equipped with mechanical stirrer, dry ice condenser, $N_2$ inlet & thermocouple, and addition funnel. MPTES and TNBA were mixed with the solvent and 257.5 g (1.58 moles) of octanoyl chloride were added slowly through the addition funnel. The slurry was water washed with 200 g 10% NaCl solution (5 min. stirring, 15 min. settling). The aqueous phase (583.4 g) was decanted. The material was vacuum stripped at 50 mm Hg. The temperature was increased very slowly to 150° C. (over a time span of 2 hrs.) and held for one hour. Recovered 289.1 g of lights and 560.0 g of stripped material as a pale yellow liquid that had been polish filtered through a 1-μm filter. The stripped material contained 92.7% 3-octanbyl-1-thiopropyl-triethoxysilane and also contained 1.4% MPTES and 2.3% heavies. The final yield was 90.0%. The lights contained 85.0% solvent, 4.1% TNBA, 3.4% MPTES, and 1.1% product.

The amine phase was recovered by adding 350.0 g of 20% NaOH solution to the aqueous phase. After 15 minutes of mixing and 15 minutes of settling, the bottom layer was decanted. Recovered 308.3 g amine phase as a colorless, clear liquid. The recovered amine phase had a purity of 92.7% and contained 4.0% product. The water level was 2530 ppm.

EXAMPLE 7

TNPA Assisted Addition of Octanoyl Chloride to MPTES with Brine Wash with Large Excess TNPA and No Other Solvent At ambient temperature, 396.3 g MPTES (1.66 moles) and 725 g TNPA were added to 2-L 4-neck round bottom flask with bottom take-off equipped with mechanical stirrer, dry ice condenser, $N_2$ inlet & thermocouple, and additional funnel. MPTES and TNPA were mixed and 257.5 g (1.58 moles) of octanoyl chloride were added slowly through the addition funnel. The addition was completed during a one-hour period and was allowed to exotherm to 73.7° C. The slurry was water washed with 200 g 10% NaCl solution (5 min. stirring, 15 min. settling). Separation was typical and began within 15–20 seconds of loss of agitation. The organic layer was slightly yellow and slightly hazy while the aqueous layer was white opaque. The organic phase was vacuum stripped at 25–35 mm Hg. The temperature was increased slowly to 150° C. and held for one hour. The product was filtered through a 1-micron filter pad. The material contained 89.2% 3-octanoyl-1-thiopropyltriethoxysilane and also contained 2.0% MPTES and 4.4% heavies. The material from a replicated experiment contained 88.0% 3-octanoyl-1-thiopropyltriethoxysilane, 2.9% MPTES, and 4.3% heavies.

EXAMPLE 8

TNPA Assisted Addition of Octanoyl Chloride to MPThS with 25% Excess TNPA and No Other Solvent At ambient temperature, 669.0 g MPTES (2.81 moles) and 488.2 g TNPA (3.41 moles) were added to 2-L 4-neck round bottom flask with bottom take-off equipped with mechanical stirrer, dry ice condenser, $N_2$ inlet & thermocouple, and additional funnel. MPTES and TNPA were mixed and 443.5 g (2.73 moles) of octanoyl chloride were added slowly through the addition funnel. The maximum reaction temperature during the addition was 74.4° C. The slurry was water washed with 276 g water (5 min. stirring, 15 min. settling). Separation was typical but slower than in Example 7. The organic phase was vacuum stripped at 25–35 mm Hg. The temperature was increased slowly to 150° C. and held for one hour. The product was filtered through a 1-micron filter pad. The product weighed 942.6 g (94.8% purity, 90% yield based on moles acid chloride). The removed lights weighed 60.8 g. The product also contained 1.9% MPTES and 1.4% heavies.

The amine phase was recovered by adding 580.0 g of 20% NaOH solution to the aqueous phase. After 15 minutes of mixing and 15 minutes of settling, the bottom layer was decanted. Recovered 377.7 g amine phase as a colorless, clear liquid. The recovered amine phase had a purity of 97.3% and contained 2.6% product. The water level was 36 ppm.

EXAMPLE 9

TNPA Assisted Addition of Propionyl Chloride to MPTES with Water/brine Wash

At ambient temperature, 312.4 g MPTES (1.31 moles), 196.6 g TNPA (1.375 moles) and 330 g VM&P naphtha were added to 2-L 4-neck round bottom flask with bottom take-off equipped with mechanical stirrer, dry ice condenser, $N_2$ inlet & thermocouple, and additional funnel. MPTES, TNPA, and the solvent were mixed and 115.7 g (1.25 moles) of propionyl chloride were added slowly through the addition funnel. The addition was completed during a 1.5-hour period during which an exotherm to 45° C. was observed. The slurry was heated to 60° C. and held for 2 hours at this temperature. The slurry was cooled to 35° C. and then water washed with 180 g 10% NaCl solution (5 min. stirring, 15 min. settling). The organic layer was clear and colorless while the aqueous layer was white opaque. The organic layer was dried with 5 g anhydrous sodium sulfate, filtered, and vacuum stripped at 25–35 mm Hg. The temperature was increased slowly to 130° C. and held for one hour. The product was filtered through a 1-micron filter pad. The material contained 94.1% 3-propionyl-1-thiopropyltriethoxysilane and also contained 3.2% MPTES and 0.9% heavies.

EXAMPLE 10

TNPA Assisted Addition of 2-ethylhexanoyl Chloride to MPTES with Water/brine Wash At ambient temperature, 396.3 g MPTES (1.66 moles), 249.7 g TNPA (1.75 moles) and 475 g VM&P naphtha were added to 2-L 4-neck round bottom flask with bottom take-off equipped with mechanical stirrer, dry ice condenser, $N_2$ inlet & thermocouple, and additional funnel. MPTES, TNPA, and the solvent were mixed and 257.5 g (1.58 moles) of 2-ethylhexanoyl chloride were added slowly through the addition funnel. The addition was completed during a one-hour period. The slurry was cooled to 35° C. and then water washed with 206 g 10% NaCl solution (5 min. stirring, 15 min. settling). The organic layer was slightly hazy and the aqueous layer was white opaque. The aqueous phase was decanted and the water wash repeated with 213 g fresh 10% NaCl solution after which the organic layer was clear. The organic phase was vacuum stripped at 35 mm Hg. The temperature was increased slowly to 130° C. and held for one hour. The product was filtered through a 1-micron filter pad. The product phase weighed 542.1 g (88.9% purity, 83.7% yield based on moles acid chloride). The removed lights weighed 406.3 g. The material contained 88.9% 3-(2-ethylhexanoyl)-1-thiopropyltriethoxysilane and also contained 4.7% MPTES and 2.5% heavies. Besides solvent, the lights contained 0.7% MPTES and 5.4% TNPA.

EXAMPLE 11

TNPA Assisted Addition of Oleoyl Chloride to MPTES with Water/brine Wash

At ambient temperature, 250.3 g MPTES (1.05 moles), 157.3 g TNPA (1.10 moles) and 365 g VM&P naphtha were added to 2-L 4-neck round bottom flask with bottom take-off equipped with mechanical stirrer, dry ice condenser, $N_2$ inlet & thermocouple, and additional funnel. MPTES, TNPA, and the solvent were mixed and 300.9 g (0.85 moles) of oleoyl chloride (technical grade, 85%) were added slowly through the addition funnel. The addition was completed during a 2.5-hour period. During the addition, the temperature was maintained at 38° C. and then heated to 60° C. and held for 2 hours. The slurry was cooled to 35° C. and then water washed with 205 g 10% NaCl solution (5 min. stirring, 15 min. settling). The organic layer was clear with an amber color and the aqueous layer was white opaque. The organic phase was dried with 15 g anhydrous sodium sulfate, filtered, and vacuum stripped at 25 mm Hg. The temperature was increased slowly to 130° C. and held for one hour. The product was filtered through a 1-micron filter pad. The product weighed 461.6 g (86.6% purity, 93.5% yield based on moles acid chloride). The removed lights weighed 275.6 g. The material contained 86.6% 3-oleoyl-1-thiopropyltriethoxysilane and also contained 0.2% MPTES and 3.2% heavies.

EXAMPLE 12

TNPA Assisted Addition of Diphenylphosphinic Chloride to MPTES with Water/brine Wash At ambient temperature, 125.2 g MPTES (0.525 moles), 78.7 g TNPA (0.55 moles) and 150 g VM&P naphtha were added to 2-L 4-neck round bottom flask with bottom take-off equipped with mechanical stirrer, dry ice condenser, $N_2$ inlet & thermocouple, and additional funnel. MPTES, TNPA, and the solvent were mixed and 118.3 g (0.50 moles) of diphenylphosphinic chloride were added slowly through the addition funnel. The addition was completed during a one-hour period. During the addition, an exotherm of 36° C. was observed. The slurry was cooled to 35° C. and then water washed with 111 g 10% NaCl solution (5 min. stirring, 15 min. settling). Separation occurred five minutes upon loss of agitation. The organic layer was slightly yellow and the aqueous layer was white opaque. The organic phase was dried with 5 g of anhydrous sodium sulfate, filtered, and vacuum stripped at 30 mm Hg. The temperature was increased slowly to 130° C. and held for 30 minutes. The product was polish filtered through a 1-micron filter pad. The product phase weighed 166.7 g and contained 87.2% 3-(diphenyloxyphosphorus)-1-thiopropyltriethoxysilane, 2.2% MPTES, and 5.9% heavies.

EXAMPLE 13

TNPA Assisted Reaction of Heptanoic Anhydride with MPTES with Water/brine Wash

At ambient temperature, 250.3 g MPTES (1.05 moles), 157.3 g TNPA (1.10 moles) and 300 g VM&P naphtha were added to 2-L 4-neck round bottom flask with bottom take-off equipped with mechanical stirrer, dry ice condenser, $N_2$ inlet & thermocouple, and additional funnel. MPTES, the amine, and the solvent were mixed and 242.4 g (1.00 moles) of heptanoic anhydride were added slowly through the addition funnel. The addition was completed during a one-hour period. During the addition, the exotherm was only 4° C. The mixture was heated to 60° C. and held at that temperature for 6 hours. The slurry was cooled to 35° C. and then water washed with 204 g 10% NaCl solution (5 min. stirring, 15 min. settling). The organic layer was colorless and the aqueous layer was white opaque. The organic phase was dried with 5 g of anhydrous magnesium sulfate, filtered, and vacuum stripped at 30 mm Hg. The temperature was increased slowly to 130° C. and held for 30 minutes. The product was polish filtered through a 1-micron filter pad. The product weighed 308.9 g and contained 33.7% of the pure triethoxy-ester, 3-heptanoyl-1-thiopropyltriethoxysilane, as well as 2.2% MPTES, and 57% eluted heavies.

EXAMPLE 14

4-methylmorpholine Assisted Addition of Octanoyl Chloride to MPTES with Water/brine Wash At ambient temperature, 250.3 g MPTES (1.05 moles), 111.3 g 4-methylmorpholine (1.10 moles) and 300 g VM&P naphtha were added to 2-L 4-neck round bottom flask with bottom take-off equipped with mechanical stirrer, dry ice condenser, $N_2$ inlet & thermocouple, and additional funnel. MPTES, the amine, and the solvent were mixed and 162.7 g (1.00 moles) of octanoyl chloride were added slowly through the addition funnel. The addition was completed during a two-hour period. During the addition, the temperature was maintained below 42° C. The slurry was cooled to 35° C. and then water washed with 201 g 10% NaCl solution (5 min. stirring, 15 min. settling). Separation was immediate upon loss of agitation. The organic layer was colorless and the aqueous layer was white opaque. The organic phase was dried with 5 g of anhydrous sodium sulfate, filtered, and vacuum stripped at 30 mm Hg. The temperature was increased slowly to 130° C. and held for 30 minutes. The product was polish filtered through a 1-micron filter pad. The product weighed 329.1 g and contained 94.8% 3-octanoyl-1-thiopropyltriethoxysilane (85.6% yield, based on moles octanoyl chloride), 2.3% MPTES, and 1.0% heavies.

EXAMPLE 15

N,N-dimethyloctylamine Assisted Addition of Octanoyl Chloride to MPTES with Water/brine Wash At ambient temperature, 125.2 g MPTES (0.525 moles), 86.5 g N,N-dimethyloctylamine (0.55 moles) and 150 g VM&P naphtha were added to 2-L 4-neck round bottom flask with bottom take-off equipped with mechanical stirrer, dry ice condenser, $N_2$ inlet & thermocouple, and additional funnel. MPTES, the amine, and the solvent were mixed and 81.3 g (0.50 moles) of octanoyl chloride were added slowly through the addition funnel. The addition was completed during a 1.5-hour period, then heated to 60° C. and held at that temperature for two hours. The slurry was cooled to 35° C. and then water washed with 103 g 10% NaCl solution (5 min. stirring, 15 min. settling). The organic layer was clear and colorless and the aqueous layer was white opaque. The organic phase was dried with 8 g of anhydrous sodium sulfate, filtered, and vacuum stripped at 12 mm Hg. The temperature was increased slowly to 130° C. and held for 30 minutes. The product was polish filtered through a 1-micron filter pad. The product phase weighed 167.5 g and contained 85.9% 3-octanoyl-1-thiopropyltriethoxysilane (78.9% yield, based on moles octanoyl chloride), 9.4% MPTES, and 2.1% heavies.

EXAMPLE 16

Pyridine Assisted Addition of Octanoyl Chloride to MPTES with Water/brine Wash

At ambient temperature, 396.3 g MPThS (1.66 moles), 137.6 g pyridine (1.74 moles) and 475 g VM&P naphtha were added to 2-L 4-neck round bottom flask with bottom take-off equipped with mechanical stirrer, dry ice condenser, $N_2$ inlet & thermocouple, and additional funnel. MPTES, the amine, and the solvent were mixed and 257.5 g (1.58 moles) of octanoyl chloride were added slowly through the addition funnel. The addition was completed during a 1-hour period. The slurry was cooled to 35° C. and then water washed with 100 g 10% NaCl solution (5 min. stirring, 15 min. settling). The organic layer was clear and colorless and the aqueous layer was white opaque. The organic phase (972.6 g) was dried with magnesium sulfate, filtered, and vacuum stripped. The temperature was increased slowly to 130° C. and held for 30 minutes. The product was polish filtered through a 1-micron filter pad. The product weighed 513.4 g and contained 85.6% 3-octanoyl-1-thiopropyltriethoxysilane (76.2% yield, based on moles octanoyl chloride), 1.6% MPTES, and 4.7% heavies.

EXAMPLE 17

TNPA Assisted Addition of Octanoyl Chloride to MPTMS with Water/brine Wash

At ambient temperature, 326.2 g MPTMS (1.66 moles), 249.7 g tri-n-propylamine (1.74 moles) and 475 g VM&P naphtha were added to 2-L 4-neck round bottom flask with bottom take-off equipped with mechanical stirrer, dry ice condenser, $N_2$ inlet & thermocouple, and additional funnel. MPTES, the amine, and the solvent were mixed and 257.5 g (1.58 moles) of octanoyl chloride were added slowly through the addition funnel. The addition was completed during a 1-hour period. The slurry was cooled to 35° C. and then water washed with 100 g 10% NaCl solution (5 min. stirring, 15 min. settling). The organic layer was clear and colorless and the aqueous layer was white opaque. The organic phase (1007.8 g) was dried with magnesium sulfate, filtered, and vacuum stripped. The temperature was increased slowly to 150° C. and held for 30 minutes. The product was polish filtered through a 1-micron filter pad. The product phase weighed 474.7 g and contained 89.9% 3-octanoyl-1-thiopropyltrimethoxysilane (83.6% yield, based on moles octanoyl chloride), 1.6% MPTMS, and 5.2% heavies.

Continuous Operation

Alternatively, the process can be run in the continuous mode. The most important factor in designing a continuous unit was the capability of handling large amounts of solid salts. The process is shown in FIG. 1. MPTES, TNPA, optionally solvent, and the acid halide were fed to the reactor. The reactor could be a plug flow reactor (PFR), a mixed flow reactor/continuous stirred tank reactor (MFR/CSTR), a combination of PFR and MFR/CSTR or a series of mixed flow reactors. The most suitable reactor design was found to be a series of CSTR's that is shown in FIG. 2. The reactants, MPTES, TNPA, octanoyl chloride, and solvent (petroleum ether) were fed to the first reactor. In this reactor, the majority of the reaction occurs. Cooling was necessary during the reaction. Reactor 2 is optional and may be used to split the octanoyl chloride feeds: Less salt and heat are generated in the first reactor resulting in better mixing in the first reactor and higher heat removal rates. Reactor 3 was necessary to drive the reaction to completion. The holding tank was used as a buffer between the reaction and the downstream part of the process.

The reaction mixture left the reactor system as a thick slurry and subsequently was combined with an aqueous stream (0–25% sodium chloride solution), then thoroughly mixed, preferably in a static mixer, and allowed to settle in a mixer settler. Two phases quickly formed, the top one was the organic phase that contained the product, solvent, if any, and free excess TNPA, the bottom one was the aqueous phase that contained TNPA hydrochloride and sodium chloride solution. The top phase was fed to a stripping column, where the product was separated from the process lights. In order to recycle the process lights, further refinement might be desirable which could be achieved in a second stripping column that was operated at a lower temperature than the first one. These higher boiling lights are one of the waste streams in the process. The recycled lights might be dried in a drying column if so desired.

The bottom phase from the first mixer settler was combined with a stream of caustic solution and than thoroughly mixed, preferably in a static mixer. The free tri-n-propylamine was formed which was only very slightly soluble in the aqueous phase. Due to this low solubility, the aqueous (bottom) phase did not require additional treatment before disposal, since tri-n-propylamine was fairly biodegradable, it could be degraded within plant-internal waste water treatment facilities. The top phase was the free amine and could be dried in a drying column, if so desired, before being returned to the process.

EXAMPLE 18

TNPA Assisted Continuous Reaction with Water/brine Wash

Two 1-L resin pots were connected in series, each equipped with electric stirrer, thermocouple, respective inlets and outlets, and nitrogen inlet. The first reactor was charged with solutions A and B, the second reactor with the reaction mixture from the first reactor. The first reactor was run in an ice bath, the second reactor did not have any provision for cooling.

| Solution A: | 1752 g | Mercaptopropyltriethoxysilane (MPTES) |
| | 1103 g | Tri-n-propylamine (TNPA) |
| | | Solvent: Isooctane |
| Solution B: | 1139 g | Octanoyl chloride |
| | | Solvent: Isooctane |

A total of 2900 ml solvent was added to both solutions such that the volumes of both solutions were equal. Hence, equal pump rates fed stoichiometrically required amounts of the reactants to the continuous reactor system. The actual amounts fed to the reactors were monitored by weight.

The reactors were allowed to reach steady-state condition (approximately after 6 residence times). Steady-state condition was also indicated by a constant temperature in the reactor. The reactor volume was 700 ml, the residence time 19.5 minutes. A self-priming pump continuously transferred the reaction mixture from the first to the second reactor. Another pump transferred the reaction mixture from the second reactor into a static mixer that was co-fed with water. The volume of the aqueous phase was approximately half the volume of the reaction mixture. The two-phase system that left the static mixer was then allowed to settle in a separation funnel.

In a time period of 20 minutes, 328.9 g of solution A (containing 0.77 moles MPTES and 0.81 moles of TNPA) and 260.2 g of solution B (containing 0.63 moles octanoyl chloride) were fed to the reactor. Recovered 472.1 g of organic phase that contained 45.4% product, 8.2% MPTES, 5.6% TNPA, 38.6% solvent, 0.5% heavies, 0.06% water and also recovered 327.9 g of aqueous phase. The aqueous phase was not further analyzed.

The organic phase contained 0.59 moles of 3-octanoyl-1-thiopropyltriethoxysilane. Hence, 92.8% of the limiting reagent, namely octanoyl chloride, was converted into product.

What is claimed is:

1. A process for making a blocked mercaptosilane, comprising the steps of: reacting mercaptosilane with organic or inorganic halide or anhydride in the presence of at least one acid acceptor to produce a slurry reaction product, wherein said acid acceptor in free form is substantially water insoluble and the respective salt of said acid acceptor is substantially water soluble washing the slurry reaction product with water or brine to produce an organic phase that comprises the blocked mercaptosilane and an aqueous phase that is immiscible with the organic phase and that comprises the respective salt of the acid acceptor.

2. The process of claim 1 wherein the acid acceptor is a tertiary amine having an aqueous solubility less than 0.2% and the respective salt is a tertiary amine hydrohalide.

3. The process of claim 1 wherein the mercaptosilane is at least one of those providing the respective blocked mercaptosilane selected from the group of 2-triethoxysilyl-1-ethyl thioacetate; 2-trimethoxysilyl-1-ethyl thioacetate; 2-(methyldimethoxysilyl)-1-ethyl thioacetate; 3-trimethoxysilyl-1-propyl thioacetate; triethoxysilylmethyl thioacetate; trimethoxysilylmethyl thioacetate; triisopropoxysilylmethyl thioacetate; methyldiethoxysilylmethyl thioacetate; methyldimethoxysilylmethyl thioacetate; methyldiisopropoxysilylmethyl thioacetate; dimethylethoxysilylmethyl thioacetate; dimethylmethoxysilylmethyl thioacetate; dimethylisopropoxysilylmethyl thioacetate; 2-triisopropoxysilyl-1-ethyl thioacetate; 2-(methyldiethoxysilyl)-1-ethyl thioacetate; 2-(methyldiisopropoxysilyl)-1-ethyl thioacetate; 2-(dimethylethoxysilyl)-1-ethyl thioacetate; 2-(dimethylmethoxysilyl)-1-ethyl thioacetate; 2-(dimethylisopropoxysilyl)-1-ethyl thioacetate; 3-triethoxysilyl-1-propyl thioacetate; 3-triisopropoxysilyl-1-propyl thioacetate; 3-methyldiethoxysilyl-1-propyl thioacetate; 3-methyldimethoxysilyl-1-propyl thioacetate; 3-methyldiisopropoxysilyl-1-propyl thioacetate; 1-(2-triethoxysilyl-1-ethyl)-4-thioacetylcyclohexane; 1-(2-triethoxysilyl-1-ethyl)-3-thioacetylcyclohexane; 2-triethoxysilyl-5-thioacetylnorbornene; 2-triethoxysilyl-4-thioacetylnorbornene; 2-(2-triethoxysilyl-1-ethyl)-5-thioacetylnorbornene; 2-(2-triethoxysilyl-1-ethyl)-4-thioacetylnorbornene; 1-(1-oxo-2-thia-5-triethoxysilylpenyl)benzoic acid; 6-triethoxysilyl-1-hexyl thioacetate; 1-triethoxysilyl-5-hexyl thioacetate; 8-triethoxysilyl-1-octyl thioacetate; 1-triethoxysilyl-7-octyl thioacetate; 6-triethoxysilyl-1-hexyl thioacetate; 1-triethoxysilyl-5-octyl thioacetate; 8-trimethoxysilyl-1-octyl thioacetate; 1-trimethoxysilyl-7-octyl thioacetate; 10-triethoxysilyl-1-decyl thioacetate; 1-triethoxysilyl-9-decyl thioacetate; 1-triethoxysilyl-2-butyl thioacetate; 1-triethoxysilyl-3-butyl thioacetate; 1-triethoxysilyl-3-methyl-2-butyl thioacetate; 1-triethoxysilyl-3-methyl-3-butyl thioacetate; 3-trimethoxysilyl-1-propyl thiooctanoate; 3-triethoxysilyl-1-propyl thiopalmitate; 3-triethoxysilyl-1-propyl thiooctanoate; 3-triethoxysilyl-1-propyl thiobenzoate; 3-triethoxysilyl-1-propyl thio-2-ethylhexanoate; 3-methyldiacetoxysilyl-1-propyl thioacetate; 3-triacetoxysilyl-1-propyl thioacetate; 2-methyldiacetoxysilyl-1-ethyl thioacetate; 2-triacetoxysilyl-1-ethyl thioacetate; 1-methyldiacetoxysilyl-1-ethyl thioacetate; 1-triacetoxysilyl-1-ethyl thioacetate; tris-(3-triethoxysilyl-1-propyl)trithiophosphate; bis-(3-triethoxysilyl-) 1-propyl)methyldithiophosphonate; bis-(3-triethoxysilyl-1-propyl)ethyldithiophosphonate; 3-triethoxysilyl-1-propyldimethylthiophosphinate; 3-triethoxysilyl-1-propyldiethylthiophosphinate; tris-(3-triethoxysilyl-1-propyl)tetrathiophosphate; bis-(3-triethoxysilyl-1-propyl)methyltrithiophosphonate; bis-(3-triethoxysilyl-1-propyl)ethyltrithiophosphonate; 3-triethoxysilyl-1-propyldimethyldithiophosphinate; 3-triethoxysilyl-1-propyldiethyldithiophosphinate; tris-(3-methyldimethoxysilyl-1-propyl)trithiophosphate; bis-(3-methyldimethoxysilyl-1-propyl)methyldithiophosphonate; bis-(3-methyldimethoxysilyl-1-propyl)ethyldithiophosphonate; 3-methyldimethoxysilyl-1-propyldimethylthiophosphinate; 3-methyldimethoxysilyl-1-propyldiethylthiophosphinate; 3-triethoxysilyl-1-propylmethylthiosulphate; 3-triethoxysilyl-1-propylmethanethiosulphonate; 3-triethoxysilyl-1-propylethanethiosulphonate; 3-triethoxysilyl-1-propylbenzenethiosulphonate; 3-triethoxysilyl-1-propyltoluenethiosulphonate; 3-triethoxysilyl-1-propylnaphthalenethiosulphonate; 3-triethoxysilyl-1-propylxylenethiosulphonate; triethoxysilylmethylmethylthiosulphate; triethoxysilylmethylmethanethiosulphonate; triethoxysilylmethylethanethiosulphonate; triethoxysilylmethylbenzenethiosulphonate; triethoxysilylmethyltoluenethiosulphonate; triethoxysilylmethylnaphthalenethiosulphonate; and triethoxysilylmethylxylenethiosulphonate.

4. The process of claim 1, wherein the organic or inorganic halide or anhydride is at least one of those providing the respective blocked mercaptosilanes selected from the group of compounds listed in claim 3.

5. The process of claim 1 wherein the organic phase further comprises an inert solvent, a portion of which is recycled from a previous run.

6. The process of claim 1 wherein the slurry reaction product is formed in the temperature range of 0–150° C. under an inert atmosphere.

7. The process of claim 1 wherein the steps are performed continuously with neutralization of said respective salt of said acid acceptor and recycle of said acid acceptor.

8. The process of claim 1 wherein the mercaptosilane is selected from 3-mercaptopropyltriethoxysilane, 3-mercaptopropylmethyldiethoxysilane, 3-mercaptopropyldimethylethoxysilane, 3-mercaptopropyltrimethoxysilane, 3-mercaptopropylmethyldimethoxysilane, and 3-mercaptopropyldimethylmethoxysilane, and the organic halide is selected from octanoyl chloride, 2-ethylhexanoyl chloride, hexanoyl chloride, decanoyl chloride, lauroyl chloride, and oleoyl chloride, and the acid acceptor is tripropylamine.

9. The process of claim 1 wherein the blocked mercaptosilane is 3-triethoxysilyl-1-propyl thiooctanoate, and the molar ratios of mercaptosilane to tripropylamine to acid chloride range from 1.00/1.05/1.00 to 1.25/5.00/1.00.

10. The process of claim 5 wherein the organic solvent is selected from the group of hydrocarbons including alkanes, isoalkanes, petroleum ethers, cycloalkanes, and aromatics.

11. The process of claim 1 wherein the blocked mercaptosilane has the formula:

$$[[(ROC(=O))_p\text{-}(G)_j]_k\text{-}Y\text{---}S]_r\text{-}G\text{-}(SiX_3)_s \qquad (1)$$

and $$[(X_3Si)_q\text{-}G]_a\text{-}[Y\text{---}[S\text{-}G\text{-}SiX_3]_b]_c \qquad (2)$$

wherein

Y is a polyvalent species $(Q)_zA(=E)$ selected from the group consisting of: —C(=NR)—; —SC(=NR)—; —SC(=O)—; (—NR)C(=O)—; (—NR)C(=S)—; —OC(=O)—; —OC(=S)—; —C(=O)—; —SC(=S)—; —C(=S)—; —S(=O)—; —S(=O)$_2$—; —OS(=O)$_2$—; (—NR)S(=O)$_2$—; —SS(=O)—; —OS(=O)—; (—NR)S(=O)—; —SS(=O)$_2$—; (—S)$_2$P(=O)—; —(—S)P(=O)—; —P(=O)(-)$_2$; (—S)$_2$P(=S)—; —(—S)P(=S)—; —P(=S)(-)$_2$; (—NR)$_2$P(=O)—; (—NR)(—S)P(=O)—; (—O)(—NR)P(=O)—; (—O)(—S)P(=O)—; (—O)$_2$P(=O)—; —(—O)P(=O)—; —(—NR)P(=O)—; (—NR)$_2$P(=S)—; (—NR)(—S)P(=S)—; (—O)(—NR)P(=S)—; (—O)(—S)P(=S)—; (—O)$_2$P(=S)—; —(—O)P(=S)—; and —(—NR)P(=S)—; each wherein the atom (A) attached to the unsaturated heteroatom (E) is attached to the sulfur, which in turn is linked via a group G to the silicon atom;

each R is chosen independently from hydrogen, straight, cyclic, or branched alkyl that may or may not contain unsaturation, alkenyl groups, aryl groups, and aralkyl groups, with each R containing from 1 to 18 carbon atoms;

each G is independently a monovalent or polyvalent group derived by substitution of alkyl, alkenyl, aryl, or aralkyl wherein G can contain from 1 to 18 carbon atoms, and if G directly bonded to Y is univalent (i.e., if p=0), G can be a hydrogen atom;

X is independently selected from the group consisting of —Cl, —Br, RO—, RC(=O)O—, R$_2$C=NO—, R$_2$NO— or R$_2$N—, —R, —(OSiR$_2$)$_t$(OSiR$_3$) wherein each R and G is as above and at least one X is not —R;

Q is oxygen, sulfur, or (—NR—);

A is carbon, sulfur, phosphorus, or sulfonyl;

E is oxygen, sulfur, or NR;

p is 0 to 5; r is 1 to 3; z is 0 to 2; q is 0 to 6; a is 0 to 7; b is 1 to 3; j is 0 to 1, but it may be 0 only if p is 1; c is 1 to 6, preferably 1 to 4; t is 0 to 5; s is 1 to 3; k is 1 to 2; with the provisos that (A) if A is carbon, sulfur, or sulfonyl, then (i) a+b=2 and (ii) k=1; (B) if A is phosphorus, then a+b=3 unless both (i) c>1 and (ii) b=1, in which case a=c+1; and (C) if A is phosphorus, then k is 2.

and the organic halide is selected from octanoyl chloride, 2-ethylhexanoyl chloride, hexanoyl chloride, decanoyl chloride, lauroyl chloride, and oleoyl chloride, and the acid acceptor is tripropylamine.

12. The process of claim 1 wherein the mercaptosilane has the formula:

$$(X_3Si)_s\text{-}G\text{-}SH$$

wherein X is independently selected from the group consisting of —Cl, —Br, RO—, RC(=O)O—, R$_2$C=NO—, R$_2$NO— or R$_2$N—, —R, —(OSiR$_2$)$_t$(OSiR$_3$) wherein each R is chosen independently from hydrogen, straight, cyclic, or branched alkyl that may or may not contain unsaturation, alkenyl groups, aryl groups, and aralkyl groups, with each R containing from 1 to 18 carbon atoms, and at least one X is not —R; G is a monovalent or polyvalent group derived by substitution of alkyl, alkenyl, aryl, or aralkyl wherein G can contain from 1 to 18 carbon atoms and s is 1 to 3; and the organic halide is selected from octanoyl chloride, 2-ethylhexanoyl chloride, hexanoyl chloride, decanoyl chloride, lauroyl chloride, and oleoyl chloride, and the acid acceptor is tripropylamine.

\* \* \* \* \*